United States Patent [19]

Jacoby

[11] Patent Number: 5,230,621

[45] Date of Patent: Jul. 27, 1993

[54] ENDOSCOPIC METHOD AND DEVICE FOR SUBGINGIVAL DENTAL PROCEDURES

[76] Inventor: Bennett Jacoby, 25283 Cabot Rd., Ste. 111, Laguna Hills, Calif. 92653

[21] Appl. No.: 816,307

[22] Filed: Dec. 26, 1991

[51] Int. Cl.$^5$ ............................................. A61C 1/00
[52] U.S. Cl. ....................................... 433/29; 433/31; 128/6
[58] Field of Search .................... 433/29, 30, 31, 72, 433/119, 86, 141, 142, 143; 128/4, 6

[56] References Cited

U.S. PATENT DOCUMENTS

| | | | |
|---|---|---|---|
| 3,297,022 | 1/1967 | Wallace | 128/6 |
| 4,170,997 | 10/1979 | Pinnow et al. | 128/395 |
| 4,208,579 | 6/1980 | Scrivo et al. | |
| 4,590,064 | 5/1986 | Gaffar | |
| 4,601,284 | 7/1986 | Arakawa et al. | |
| 4,790,751 | 12/1988 | Reinhardt et al. | 433/29 |
| 4,858,001 | 8/1989 | Milbank et al. | |
| 4,880,619 | 11/1989 | Gaffar | |
| 4,917,603 | 4/1990 | Haack | 433/29 |
| 5,016,098 | 5/1991 | Cooper et al. | 358/98 |
| 5,051,823 | 9/1991 | Cooper et al. | 433/26 |
| 5,052,924 | 10/1991 | Berg | 433/114 |

FOREIGN PATENT DOCUMENTS 0389453 9/1990 European Pat. Off. ............... 128/6

OTHER PUBLICATIONS

*Dorland's Illustrated Medical Dictionary*, Twenty-sixth edition, p. 442.

Reinhardt, R. A., Johnson, G. K., and Dubois, L. M., Clinical Effects of Closed Root Planing Compared to Papilla Reflection and Fiber Optic Augmentation, J. Periodontol, May 1991, pp. 317–321.

Immunity Steel Instruments, Hu-Friedy catalog, pp. 21–38.

Primary Examiner—Cary E. O'Connor
Attorney, Agent, or Firm—Robert D. Buyan

[57] ABSTRACT

A device and method for removing deposited material from subgingival tooth surfaces, under endoscopic guidance, without surgical cutting of the gingiva. In one embodiment, the invention comprises a simple endoscopic probe insertable into the gingival sulcus to endoscopically visualize the process of and/or effects of subgingival root planing, scaling or other plaque removal procedures carried out by other operative instruments. In another embodiment, the endoscopic viewing apparatus is incorporated into an operative instrument which is, in itself, usable to effect removal deposited material from subgingival tooth surfaces such that the operator may endoscopically view and/or guide the instrument while using the instrument itself to effect the removal of material deposited on the subgingival tooth surfaces. The invention includes methods for removing deposited material from subgingival tooth surfaces under endoscopic guidance and/or monitoring.

80 Claims, 5 Drawing Sheets

ENDOSCOPIC METHOD AND DEVICE FOR SUBGINGIVAL DENTAL PROCEDURES

FIELD OF THE INVENTION

The present invention relates generally to dental equipment. More particularly the invention relates to an apparatus and method for endoscopic viewing, without the need for surgical incision and/or excision of the gum, of subgingival tooth surfaces or subgingival tissues. The invention is operative to permit visualization, guidance, monitoring, and/or assessment of any type of treatment procedure directed to the subgingival tooth surfaces or periodontium including, but not limited to, subgingival plaque and calculus removal procedures.

BACKGROUND OF THE INVENTION i. Pathogenesis of Periodontal Disease

Periodontal disease encompasses a group of different disorders which affect the gums or supporting structures of the teeth. The general epidemiology of plaque associated periodontal disease typically begins with the formation of supragingival microbial plaque which, if left untreated, subsequently invades the normally closed space between the free gingiva and the tooth surface. If left unremoved, such subgingival plaque gives rise to the formation of hardened calculi and areas of erosion on the subgingiva surfaces of the tooth (i.e. the subgingival enamel and root surfaces). Resultant inflammation of the surrounding tissues and recession of the surrounding connective tissue and bone then occurs. Such inflammation and recession of the periodontia results in the formation of a gap or "periodontal pocket" between the gingival tissue and the adjacent tooth surface. The gradual loss of ligamentous attachment and surrounding alveolar bone mass in periodontal disease often results in loss of the affected tooth, unless effective treatment is administered to halt the progression of the disease.

Clinically, plaque associated periodontal disease may be treated by either a surgical or nonsurgical approach.

The surgical approach to the treatment of plaque associated periodontal disease typically involves the performance of one or more surgical procedures whereby the gingival tissue is excised and the underlying tooth surfaces (e.g. subgingival enamel and a portion of the root) are visually examined and subjected to scaling and root planing under direct visualization. Although the surgical approach to the treatment of plaque associated periodontal disease is often highly effective, such surgical approach is also associated with significant expense and a significant degree of patient discomfort.

The nonsurgical approach to the treatment of plaque associated periodontal disease typically involves procedures known as subgingival scaling and root planing. Some chemical formulations for dissolving and/or removing subgingival plaque and/or calculus are also known. Subgingival scaling and root planing procedures are typically accomplished by inserting a hand instrument, an ultrasonic or sonic cleaning device and/or a rotating instrument into the periodontal pocket (PP), without cutting or excising the gingiva, for the purpose of scraping plaque or dental calculus from the subgingival tooth surfaces. The ultimate effectiveness of such subgingival scaling and root planing procedures, or chemical plaque/calculus removal methods, is dependent upon the completeness with which removal of plaque or calculi has been effected by such procedures.

Because the surrounding gingiva remain intact, the operator is unable to directly view the subgingival tooth surfaces when carrying out such subgingival plaque and calculus removal procedures. The inability to visualize the subgingival tooth surfaces makes it virtually impossible for the operator to ascertain whether all of the subgingival plaque or calculus has been effectively removed. Failure to completely remove all subgingival deposits of plaque or dental calculus may result in progression of the periodontal disease. Such progression of the disease often necessitates abandonment of the nonsurgical treatment approach in favor of the more costly and painful surgical approach.

In view of the desirability of treating periodontal disease by nonsurgical treatment modalities, there exists a need in the art for new devices and techniques whereby the subgingival tooth surfaces may be endoscopically viewed to permit visual assessment and/or guidance of subgingival plaque/calculus removal procedures without the need for surgical cutting or excision of the gums.

Additionally, there exists a need in the art for endoscopically viewing the subgingival tooth surfaces and/or subgingival tissues of the periodontium during and/or after various treatment procedures directed at the subgingival tooth surfaces and/or subgingival tissues. Examples of treatment procedures which may guided, monitored, visualized and/or assessed by direct endoscopic viewing include (a) resection of subgingival granulation tissue, (b) alveolar bone seeding or bone grafting procedures, and (c) the application of chemical agents to the subgingival root surfaces to facilitate new ligamentous attachment thereto.

ii. Instruments Utilized for Subgingival
Scaling and Root Planing Procedures

The instruments used for subgingival scaling and root planing procedures include (a) hand instruments, (b) ultrasonic instruments; (c) sonic instruments; and (d) rotating instruments.

Hand Instruments

The hand instruments used for scaling and root planing typically comprise three parts: (a) the working part or blade; (b) the shank; and (c) an elongate handle. The working part or blade portion of the instrument may be in the form of a curette, sickle, hoe, chisel or file and is typically formed of hard material such as carbon steel, stainless steel or tungsten carbide. The "shank" portion of the instrument is typically continuous with or attached to the working part or blade and is of sufficiently small diameter to be insertable, along with the working part or blade, into the subgingival sulcus or pocket. The "handle" portion is typically 3-6 inches in length and substantially larger in cross-sectional dimension than the shank portion of the instrument.

In carrying out subgingival scaling and root planing procedures deep within the subgingival sulcus or pocket, the most commonly used working part or blade is that of a "curette" or "hoe". The "curette" blade typically comprises a rigid blade member having a generally concave leading surface with two lateral cutting edges. The length and angulation of the shank, as well as the specific dimensions of the curette blade, differ depending on the instrument manufacturer and the specific intended application of the instrument.

The "hoe" blades typically comprise a single cutting edge disposed at an approximate 100° angle to the shank of the instrument. The cutting edge may be bevelled at an approximate angle of 45°, thereby forming a "hoe" which may be pulled across the subgingival root surface.

Working parts or blades in the form of sickles, chisels and files are also used in subgingival scaling and root planing, but are used less frequently than the "curettes" and "hoes" described hereabove.

Ultrasonic Instruments

The ultrasonic instruments heretofore used for removal of subgingival plaque and/or calculus include those available commercially known as the Cavitron TM manufactured by Dentsply, York, Pa.; Le Clean Machine TM manufactured by Parkell, Farmingdale, N.Y.; and Young Ultra Scaler TM manufactured by Young Dental, Earth City, Mo. Such ultrasonic instruments typically comprise an elongate handle portion having an ultrasonic head which is sized and configured for insertion into the subgingival sulcus or pocket. An ultrasonic transducer and signal generator are operatively connected to the instrument to cause ultrasonic vibration of the ultrasonic tip. Water or saline solution may be passed through at least some ultrasonic instruments to effect cooling of the vibrating ultrasonic tip.

Such ultrasonic instruments are seldom used alone and are typically used in conjunction with one or more of the conventional hand instruments described above.

Sonic Instruments

Sonic instruments may also be used for removal of subgingival plaque and/or calculus. Examples of commercially available sonic instruments for removing plaque and/or calculus are the Titan TM manufactured by Star, Philadelphia, Pa. and Sonicflex Scaler TM manufactured by KaVo, Hoffman, Ill. Such sonic instruments typically comprise an elongate handle portion having a treatment head or tip which is sized and configured for insertion into the subgingival sulcus or pocket. A source of sonic energy is operatively connected to the instrument to cause sonic vibration of the treatment head or tip.

Like the ultrasonic instruments, sonic instruments are seldom used alone and are typically used in conjunction with one or more conventional hand instruments of the type described hereabove.

Rotating Instruments

Certain rotating instruments such as a rotating triangular diamond tip may also be used to remove plaque or calculi from hard to reach depressions such as root grooves and furcation areas on the root surface. As with the ultrasonic instrumentation, these rotating instruments are seldom used alone and are typically employed in conjunction with one or more of the conventional hand instruments described above.

iii. Chemical Methods for Removing Subgingival Plaque and/or Dental Calculus

In addition to instruments for conducting physical scaling and root planing procedures, the prior art has included chemical formulations and methods for dissolving and/or removing subgingival plaque and/or dental calculus. Examples of chemical plaque and/or calculus removing formulations are contained in U.S. Pat. No. 4,590,064 (Gaffar) entitled ANTICALCULUS ORAL COMPOSITION and U.S. Pat. No. 4,880,619 (Gaffar) entitled ANTICALCULUS ORAL COMPOSITION.

As with the physical scaling and root planing procedures, the ultimate successfulness of these chemical methods in disrupting the progress of periodontal disease depends on the completeness with which such chemical methods effect removal of subgingival plaque and/or dental calculus. Thus, it is difficult to visually verify the efficacy of such methods in cases where there has been no cutting or excision of the gingiva as to permit direct visualization of the subgingival tooth surfaces.

iv. Prior Art Devices for Illuminating Structures Within the Oral Cavity

Dental operating rooms typically are provided with adjustable overhead lights for illumination of the oral cavity during dental procedures. In addition to the typical external lighting employed in dental operating areas, the prior art includes at least one fiber optic instrument for projecting illuminating light on or into structures within the oral cavity. Such fiber optic illuminating apparatus is described in U.S. Pat. No. 4,790,751 (Reinhardt et al.), entitled DENTAL VIEWING APPARATUS AND METHOD. The apparatus of U.S. Pat. No. 4,790,751 is a dental probe or instrument having a fiber optic light transmission means extending therethrough. The fiber optic light transmission means is operative to supply illuminating light to confined areas within the oral cavity such as the dental root, pulp chamber or other constricted areas. The apparatus of U.S. Pat. No. 4,790,751 may include a blade-shaped retractor for retracting gingival tissue or other oral soft tissue. Also, the apparatus may include passageways for infusing air and/or liquid to the area upon which work is being done. The apparatus of U.S. Pat. No. 4,790,751 does not incorporate any fiber optic image transmission means for directly endoscopically visualizing areas within the oral cavity. Rather, the apparatus of U.S. Pat. No. 4,790,751 utilizes optional adjustable mirror(s) attached to the body of the apparatus to assist the dentist in indirectly visualizing structures which have been illuminated by the apparatus.

v. Prior Art Endoscopic Instruments

Many types of medical endoscopes are known in the prior art. Endoscopy has become an established technique for viewing various internal structures of the body which are not otherwise viewable absent invasive surgical excision.

The endoscope typically comprises an elongate flexible body having an optical head or image capturing means at its distal end and a handle or a manipulating means at its proximal end. Various lenses, a fiber optic cable light source and a camera are typically disposed within the endoscope body. The camera is usually located in the proximal end or outside of the endoscopic device since the camera is often times larger than the anatomical passageway duct or opening into which the endoscope is inserted. Video imaging equipment utilized in conjunction with the endoscope includes video processing electronic devices, video monitors and/or video recorders which are capable of processing and displaying the video information received into the optical head of the endoscope and transmitted to the proximal end of the endoscope by fiber optic means.

The endoscopes of the prior art have been adapted for and utilized in many specific applications including arthroscopy, laparoscopy, colonoscopy, etc.

Dental applications of endoscopic instruments have heretofore included an electronic video dental camera described in U.S. Pat. No. 5,016,098 (Cooper et al.) and a modular endoscopic apparatus with image rotation capability described in U.S. Pat. No. 4,858,001 (Milbank et al.).

The device described in U.S. Pat. No. 5,016,098 (Cooper et al.) comprises a video dental camera device having a handle and photographic head positionable within the oral cavity to permit viewing of various structures within the oral cavity. The camera head of the COOPER device may be positioned at an angle relative to an elongate handle similar to the angled configuration of prior art dental mirrors. The image receiving means of the camera may include fiber optic tubes or one or more rod lens assemblies. The handle of the instrument may incorporate a lumen for transporting fluids. The COOPER dental camera may be attached to or formed as an integral part of another dental instrument such as a dentist drill.

The device described in U.S. Pat. No. 4,858,001 (Milbank et al.) comprises a hand-held endoscopic apparatus having (a) a body; (b) a camera; and (c) a removable and interchangeable objective element capable of presenting an image of an object to the camera. The camera is rotatable mounted within the body to allow rotation of the image presented for viewing. One embodiment of the MILBANK endoscopic device incorporates an operative tip of small diameter so as to be positionable in a root canal or similarly sized dental opening.

Additionally, a fiber optic laser instrument for dental applications has been described in U.S. Pat. No. 4,170,997 (Pinnow et al.) and a fiber optic light transmitting means for dental instruments has been described in U.S. Pat. No. 4,208,579 (Scrivo et al.).

The means by which fiber optic endoscopic devices may be connected to video signal processing means for displaying endoscopic images on monitoring equipment is described in U.S. Pat. No. 4,601,284 (Arakawa et al.), the entire disclosure of which is expressly incorporated herein by reference.

No prior endoscopic apparatus is known to be sized, configured and/or adapted for insertion into, and direct endoscopic viewing of, the subgingival tooth surfaces and/or subgingival tissues within the gingival sulcus or periodontal pocket.

Accordingly, there exists a need in the art for a dental endoscopic instrument which may be inserted into the gingival sulcus or periodontal pocket and which may be utilized to endoscopically visualize the subgingival tissues and/or subgingival tooth surfaces without excision of the adjacent gingiva.

SUMMARY OF THE INVENTION

The present invention overcomes some or all of the shortcomings of the prior art by providing an endoscopic viewing apparatus device which is insertable into the subgingival sulcus or periodontal pocket to enable the operator to view the subgingival tissues and/or tooth surfaces, without the need for surgical excision or cutting of the gingiva. The apparatus of the present invention is useable to visually guide, monitor and/or assess various subgingival treatment or surgical procedures including, but not limited to, procedures for treatments for removing deposited material (e.g., plaque, calculus) from subgingival tooth surfaces.

In accordance with the invention, a fiber optic endoscopic viewing apparatus may be incorporated into or onto the body of any (a) hand instrument, (b) sonic instrument, (c) ultrasonic instrument, (d) rotating instrument, or (e) other type of instrument utilized to remove plaque and calculus from subgingival tooth surfaces. The typical hand instrument in which the endoscopic viewing apparatus is incorporated comprises (a) an elongate handle; (b) a shank extending forward from the distal end of said elongate handle; and (c) a working part or blade disposed on said shank and configured to physically scrape or otherwise remove deposits of plaque or calculus from tooth surfaces. The specific configurations in which the blade or working part may be formed include those known in the dental art as curettes, sickles, hoes, chisels or files. The endoscopic viewing apparatus of the present invention may comprise bundles of optical fibers attached to or positioned within the handle or shank portions of the instrument. In some embodiments it is desirable that the entire endoscopic viewing apparatus be contained and positioned within the normal envelope of outer surfaces of a standard plaque/calculus removing instrument so as not to create surface projections or appendages extending from the instrument as could traumatize tender gingival tissue and/or interfere with handling of the instrument.

Still further in accordance with the invention, the endoscopic viewing apparatus of the present invention may comprise any presently known or hereafter invented means for (a) transmitting illuminating light into the sulcus or periodontal pocket and (b) receiving and transmitting an optical image from the interior of the gingival sulcus or periodontal pocket to an eyepiece, video monitor or other image displaying device positioned outside of the patient's body. Such endoscopic viewing apparatus may comprise a plurality of optical fibers which extend through the handle and shank portions of the instrument and which terminate distally in viewing and illumination port(s) or an optical viewing-/illumination head. The viewing/illumination port(s) or optical head may be positioned adjacent the working part or blade of the instrument and aimed at an angle which will permit illumination and endoscopic visualization of an area immediately in front of the leading edge of the working part or blade of the instrument such that the operator may visually observe the region of the subgingival root surface whereupon the scaling and root planing procedure is being conducted.

Still further in accordance with the invention, the endoscopic viewing apparatus of the foregoing description may be incorporated into an ultrasonic or sonic instrument of the type used to remove subgingival plaque or calculus to enable the operator to view the subgingival tooth surface while performing subgingival plaque or calculus removal procedures using such ultrasonic or sonic instrument.

Still further in accordance with the invention, the endoscopic viewing apparatus of the foregoing description may be incorporated into a rotating subgingival scaling and root planing instrument such that the operator may view the subgingival tooth surface during subgingival scaling and root planing procedures carried out by such rotating instrument.

Still further in accordance with the invention, the endoscopic viewing apparatus of the foregoing description ay be incorporated into a simple subgingival endoscopic probe which is sized and configured for insertion into the gingival sulcus or periodontal pocket to permit visualization of the subgingival tooth surfaces. Such endoscopic probe is not, in itself, a dental instrument usable to remove subgingival plaque or calculus. Rather, such endoscopic probe is usable in conjunction with other instruments or chemical formulations for removing subgingival plaque or calculus. Such endoscopic probe of the invention may comprise a simple elongate probe member having an endoscopic viewing apparatus (e.g. bundles of optical fibers and lens means) for (a) passing illuminating light into the gingival sulcus or periodontal pocket and (b) receiving and transmitting an optical image from the interior of the gingival sulcus or periodontal pocket to a location outside of the patient's body whereat such image may be viewed through an attendant eyepiece, video monitor or other image viewing device. In a more complex embodiment, the subgingival endoscopic probe of the invention may be provided with multiple illumination outlet ports and/or image receiving ports/lens so as to permit illumination and/or viewing of the interior of the subgingival sulcus or periodontal pocket from numerous locations or vantage points.

Any endoscopic instrument or subgingival endoscopic probe of the present invention may be provided with one or more dilator projections or dilator members extending from the probe or instrument so as to dilate or spread the gingiva away from the adjacent tooth surfaces. Such dilator projections or members will serve to create a space between the gingiva and the tooth surfaces wherein the endoscopic viewing apparatus of the present invention may openly view the tooth surfaces as desired. Such dilator projection or member will serve to facilitate use of the endoscopic instruments and/or endoscopic probes of the invention even in cases where the gingiva is pressing against or abutting the adjacent tooth surfaces.

Any endoscopic instrument or subgingival endoscopic probe of the present invention may incorporate one or more fluid infusion passageways may be formed in any instrument or probe of the present invention to permit infusion of fluid (e.g., water, saline solution, disinfectant solutions, anticalculus solutions, solutions containing topically active anesthetic solutions, air, etc.) into the periodontal pocket or crevice.

Any endoscopic instrument or subgingival endoscopic probe of the present invention may incorporate one or more aspiration lumens may be formed in any instrument or probe of the present invention to permit aspiration of fluid and debris from the periodontal pocket or crevice.

Any endoscopic instrument or subgingival endoscopic probe of the present invention may incorporate one or more instrument passage lumens or passageways may be formed in any instrument or probe of the present invention to permit insertion, manipulation and withdrawal of one or more small surgical instruments, through the instrument or probe, into the periodontal pocket or sulcus.

Any endoscopic instrument or subgingival endoscopic probe of the present invention may incorporate one or more fiber optic bundles or other laser energy transmission passageways for passing laser energy through the body of the instrument and for projecting said laser energy onto tooth surfaces or tissues within the periodontal pocket or sulcus.

Still further in accordance with the invention there is provided a method for removing deposited material from subgingival tooth surfaces, (e.g., performing subgingival scaling and root planing procedures), said method comprising at least the steps of (a) inserting an endoscopic viewing device (e.g. an instrument or probe having an endoscopic viewing apparatus incorporated therein) into the subgingival sulcus or periodontal pocket (i.e., between the subgingival tooth surfaces and the adjacent gingiva) and (b) utilizing such endoscopic viewing device to view the subgingival tooth surfaces. The endoscopic device may be employed to facilitate and guide the performance of, and/or to verify the results of the operative material removal procedure(s).

Further objects and advantages of the invention will become apparent to those skilled in the art upon the reading and understanding of the following detailed description and the accompanying drawings.

BRIEF DESCRIPTION OF THE DRAWINGS

FIG. 1b is a schematic diagram of a portion of the human periodontal anatomy exhibiting the effects of plaque associated with periodontal disease.

FIG. 8 is a perspective view of a blunt tip endoscopic probe instrument of the invention having multiple optical image receiving ports inserted in a periodontal pocket.

FIG. 9 is a longitudinal-sectional view through line 9—9 of FIG. 7a

DETAILED DESCRIPTION OF PREFERRED EMBODIMENTS

The following detailed descriptions and the accompanying drawings are provided for purposes of illustrating and describing presently preferred embodiments of the invention and are not intended to limit the scope of the invention in any way.

Figures 1, 1A, 2, 2A:
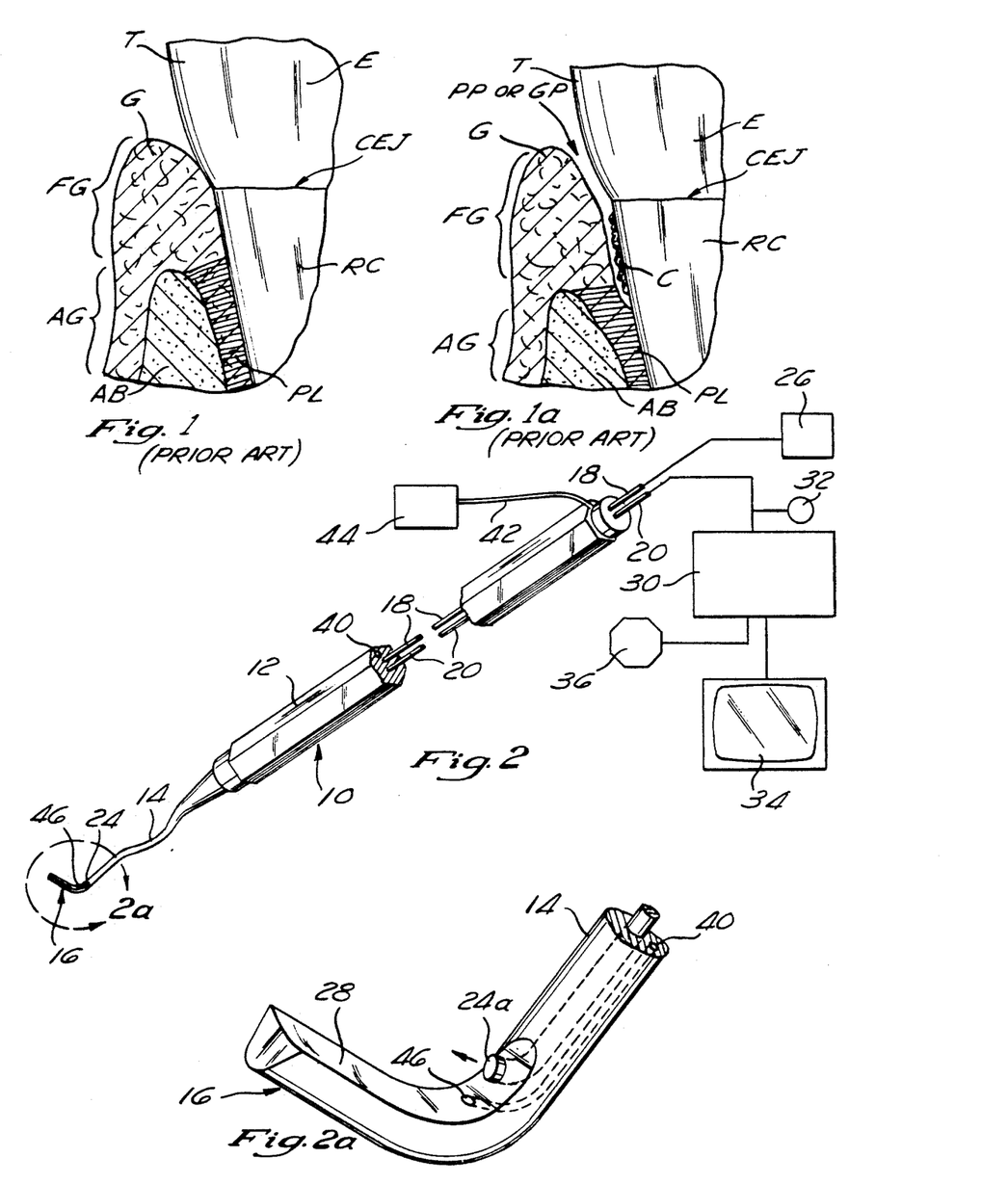
FIG. 1a is a schematic diagram of a portion of the normal human periodontal anatomy.
FIG. 2 is a perspective view of one embodiment of a subgingival hand curette instrument of the present invention.
FIG. 2a is an enlarged view of the distal shank and blade portions of the instrument shown in FIG. 2.

FIG. 1a shows the normal, undiseased periodontal anatomy of an adult human being. FIG. 1b shows the periodontal anatomy of an adult human being who suffers from periodontal disease.

The outer surface of the tooth T comprises enamel E and root cementum RC. The dividing line between the enamel E and the root cementum RC is termed the cemento-enamel junction CEJ.

The gum or gingiva G is anatomically divided into two portions—the attached gingiva AG and the free gingiva FG. The alveolar process of the mandible or "alveolar bone" AB is positioned adjacent the root of the tooth T. The periodontal ligament PL connects the tooth T to the alveolar bone AB.

Under normal non-pathological conditions, as illustrated in FIG. 1a, the free gingiva FG lies against the outer surface of the tooth T and extends slightly beyond the cemento-enamel junction CEJ, thereby fully covering and protecting the root cementum RC. Also, under normal conditions, the periodontal ligament PL forms a firm ligamentous attachment between the alveolar bone AB and the tooth T, thereby holding the tooth firmly in place.

When affected by significant periodontal disease, as illustrated in FIG. 1b, subgingival deposits of microbial plaque and dental calculus C form on the surface of the root cementum RC. The free gingiva FG becomes inflamed and begins to recede away from the tooth T, thereby creating a gap or space GP between the gingiva G and the tooth T. Such gap or space GP is known as a gingival sulcus or periodontal pocket. If the subgingival plaque or calculus C is not effectively removed, its continued presence will give rise to inflammatory and-/or immunological process within the gingiva with a corresponding gradual loss of the periodontal ligament PL and regression of the alveolar bone AB. Such loss of the ligamentous and bony support may ultimately result in loosening and loss of the tooth.

In order to facilitate removal of subgingival plaque or calculus C, the present invention provides a method and device for visualizing the subgingival tooth surfaces without the need for surgical excision of the surrounding gingiva G. The device of the present invention comprises an endoscopic looking device such as a fiber optic image transmitting means which is directly insertable into the gingival sulcus or periodontal pocket to transmit a visual image of the subgingival tooth surfaces to an eyepiece or video monitor positioned outside the patient's body. The device of the present invention thereby enables the operator to visually guide, monitor and/or assess the efficacy of the plaque or calculus removing treatment. The endoscopic looking device or fiber optic image transmission means of the present invention may be incorporated into the body of an instrument used for carrying out subgingival scaling and root planing procedures. Examples of the types of instruments into which the endoscopic looking device or fiber optic means of the present invention may be incorporated include any and all of the instruments typically utilized for performing subgingival scaling and root planing procedures. In particular, specific embodiments of the invention may be incorporated into a hand instrument (e.g. a curette, sickle, chisel, file or hoe) or an ultrasonic or sonic instrument of the type typically utilized to remove subgingival plaque and dental calculus C. Examples of these specific embodiments of the invention are described in specific detail herebelow and shown in the accompanying drawings.

i. A Hand Instrument

As shown in FIGS. 2 and 2a, one embodiment invention comprises a hand instrument for carrying out subgingival scaling and root planing procedures. Such hand instrument 10 comprises a handle 12, a shank 14 and a working part or blade 16. A first optical fiber group or bundle 18 and a second optical fiber group or bundle 20 extend longitudinally through the handle portion 12 and shank portion 14 of the instrument 10. In the embodiment shown, the first optical fiber bundle 18 comprises light transmitting optical fibers. The second optical fiber bundle 20 comprises image transmitting fibers.

Both the first 18 and second 20 optical fiber bundles are attached to and terminate within a distal illuminating/image receiving apparatus or optical head 24. Such optical head 24 may be positioned on the shank portion 14 of the instrument, immediately adjacent the working part or blade 16 thereof. A lens or image receiving port is formed on the optical head, adjacent or in contact with at least the second (image receiving) optical fiber bundle 20 to receive and collect the optical image to be endoscopically viewed.

The proximal end of the first (illuminating) fiber bundle 18 is connectable to an external light source 26 such that illuminating light may be conveyed and transported by the first (illuminating) optical fiber bundle 18 through the handle portion 12 and shank portion 14 of the instrument 10 such that illuminating light will emanate from the optical head 24. The optical head 24 may be aimed or positioned relative to the working part or blade 16 of the instrument such that the illuminating light will be cast on and ahead of or in front of the leading surface 28 of the working part or blade 16. Examples of such aiming or positioning of the optical head toward the leading edge of the working part or blade 16 is specifically shown as elements 24a and 24b on FIGS. 2, 2a, 2b, 4 and 4a. Such positioning of the optical head 24a, 24b ahead of or adjacent the leading edge 28 of the working part or blade 16 permits the operator to endoscopically view the plaque and/or calculus removal being effected by the leading edge 28 of the working part or blade 16 of the instrument 10. Additionally, such positioning of the optical head 24a, 24b ahead of the leading edge 28 of the working part or blade 16 may permit the operator to view a sufficient region of tooth surface ahead of the leading edge 28 to assess the severity of plaque and/or calculus deposits being treated and to guide the use of the instrument 10 in a manner which effectively removes the entirety of such plaque or calculus deposits.

Figures 2B, 2C:
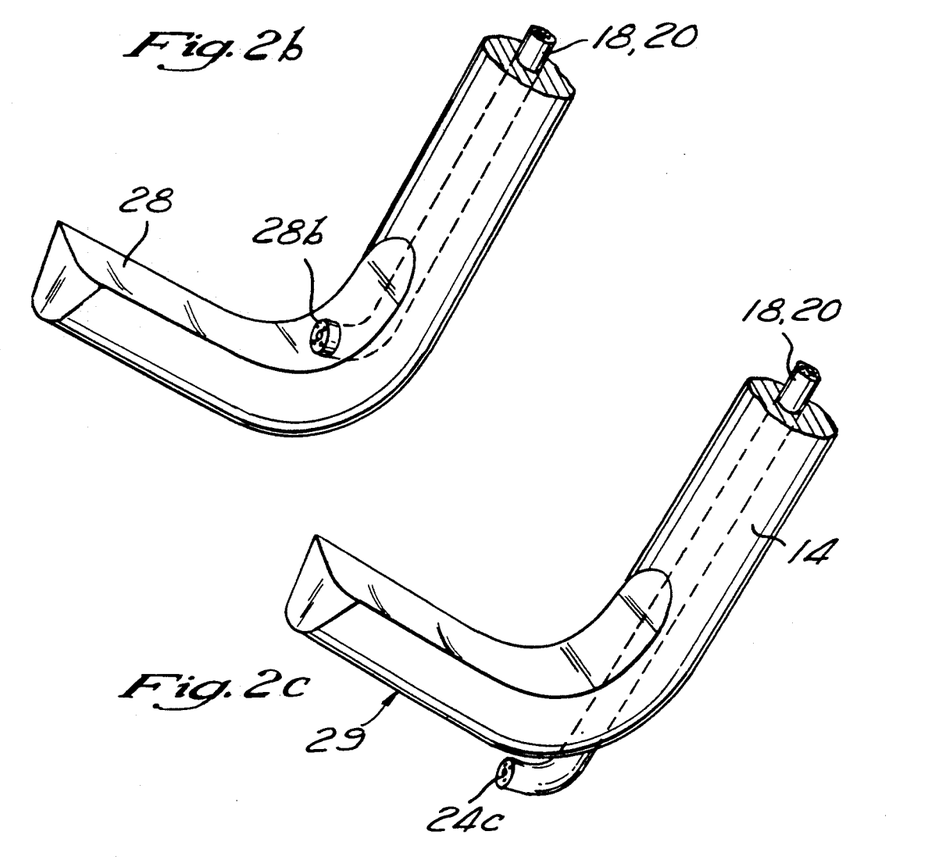
FIG. 2b is an enlarged view of the distal shank and blade portions of an alternative embodiment of the instrument shown in FIG. 2 wherein the optical head is positioned immediately adjacent the leading edge of the blade.
FIG. 2c is an enlarged view of the distal shank and blade portions of another alternative embodiment of the instrument shown in FIG. 2 wherein the optical head is positioned beneath the bottom of the blade portion of the instrument.
Figure 4A:
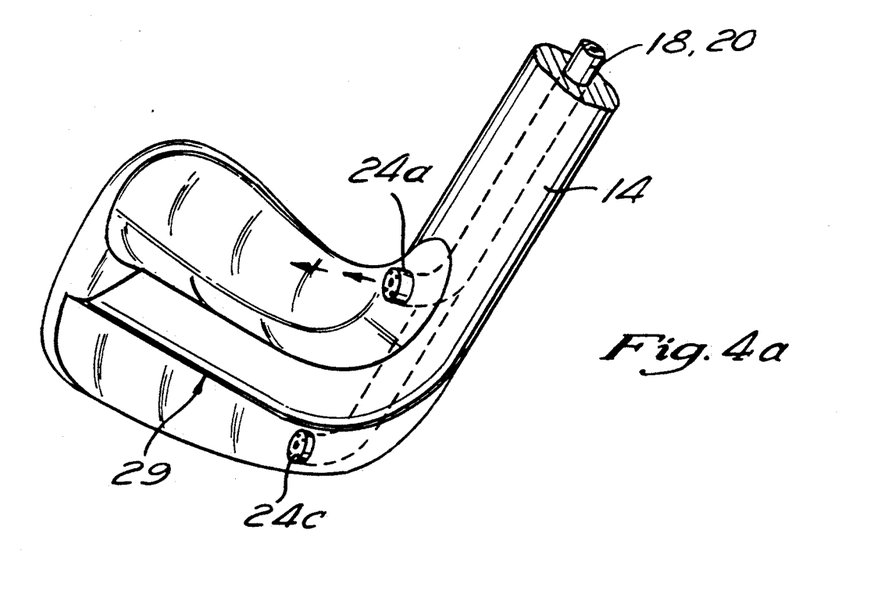
FIG. 4a is a perspective view of a modified version of the instrument shown in FIG. 4 having both upper and lower optical heads and incorporating both upper and lower gingival tissue dilator members.

Alternatively or additionally, an image receiving and/or illuminating optical head 24c may be positioned adjacent the underside of the working part or blade 16 as shown in FIGS. 2c and 4a. Such alternative or additional positioning of an optical head 24c adjacent the underside 29 of the working part or blade 16 of instrument 10 will enable the operator to (a) assess the severity of plaque and/or calculus deposits existing beneath the working part or blade 16 of the instrument 10 and (b) ascertain whether the working part or blade 16 of the instrument has been fully bottomed out in the gingival sulcus or periodontal pocket PP so as to make certain that even the deepest subgingival plaque and/or calculus is removed by the plaque/calculus removal treatment. In embodiments where two or more image receiving lenses or optical head 24 are positioned on the instrument 10, an electronic switching apparatus may be incorporated into the device or into the video imaging device positioned outside the body to permit the operator to switch back and forth between images receives by the separate optical heads 24. Alternatively, in embodiments where multiple optical heads 24 are positioned on the instrument 10, multiple image viewing devices or video monitors may be employed to simultaneously display images received separately by the multiple lenses or image receiving heads 24.

The proximal end of the second (image transmitting) optical fiber bundle 20 is operatively connectable to a solid state video-imaging device 30 such as a video monitor or television monitor and/or an eye piece 32.

The eye piece 32 may comprise any suitable optical eye piece for receiving and viewing an optical image transmitted by the second image transmitting fiber bundle 20.

The imaging device 30 may comprise any presently or hereafter known video signal processing device capable of accepting visual image information transmitted through the second image transmitting optical fiber bundle 20 and converting such visual image information to a video signal. The video signal generated by the imaging device 30 may then be shown on a video monitor 36 connected to such imaging device 30. Additionally or alternatively, the video signal generated by the imaging device 30 may be recorded on a recording device 34 operatively connected to such imaging device 30 or image-viewing device.

Magnifying apparatus or lenses may be positioned anywhere in the device of the present invention, including at the illumination/viewing port or head 24 and/or within the image processing device 30 and/or within the eye piece 32. Such magnifying apparatus' or lenses are preferably configured and positioned to effect sufficient magnification of the image transmitted by the second (image transmitting) optical fiber bundle 20 to enable the operator to easily view the subgingival tooth surfaces. It is preferable that the degree of magnification effected by any such magnifying apparatus be adjustable by the operator of the device within the range of $1\times-150\times$.

Focusing optics of the type known and utilized in the art of endoscopic devices may be incorporated within the imaging device 30 and/or eye piece 32 to permit the operator to adjust the optical focus of the image being viewed.

An optional infusion fluid lumen 40 may extend longitudinally through the handle 12 and shank 14 portions of the instrument 10. Such optional infusion fluid lumen 40 may be connected at its proximal end, by way of tubing 42, to a source or pressurized infusion fluid or a pump 44. Such optional infusion fluid lumen 40 is fluidly connected to one or more infusion fluid outflow apertures or ports 46 formed in the distal portion of the shank 14 and/or in the blade portion 16 of the instrument 10. Such infusion fluid outflow ports 46 may be formed within the optical head 24 or may be positioned apart from the optical head 24 as shown in FIG. 2. The fluid source or pump 44 may be intermittently or continuously operated by the operator of the device to pass water or other fluid through tube 42, through lumen 40, and out of outflow port 46. Such passage of water or other fluid may be utilized to accomplish periodic or continuous washing or lavage of the periodontal pocket PP during operative use of the instrument 10, thereby clearing blood and debris from the visualized field ahead of the working part or blade 16 of the instrument 10. Such washing or lavage within the periodontal pocket will facilitate the endoscopic visualization of the subgingival tooth surfaces as desired, as well as causing distension of the pocket by insufflation with the infused fluid. Such lumen 40 and ports 46 may alternately be attached to a suction source for aspiration fluid and/or debris out of the periodontal pocket.

In some embodiments, an optional additional (i.e., apart from the infusion lumen 40) aspiration lumen (not shown) attachable to a suction source or external aspiration device may also be formed longitudinally through the instrument 10 to effect suction or aspiration of fluid and/or debris from the periodontal pocket during operation of the device.

The illumination projecting and image receiving optical head 24 of the instrument 10 may be constructed or configured in any suitable way consistent with the presently or hereafter known technology of forming an endoscopic image receiving lens or port. Examples of optical head configurations are shown in FIGS. 3a and 3b respectively.

Figures 3A, 3B, 4, 5, 6A, 6B, 6C:
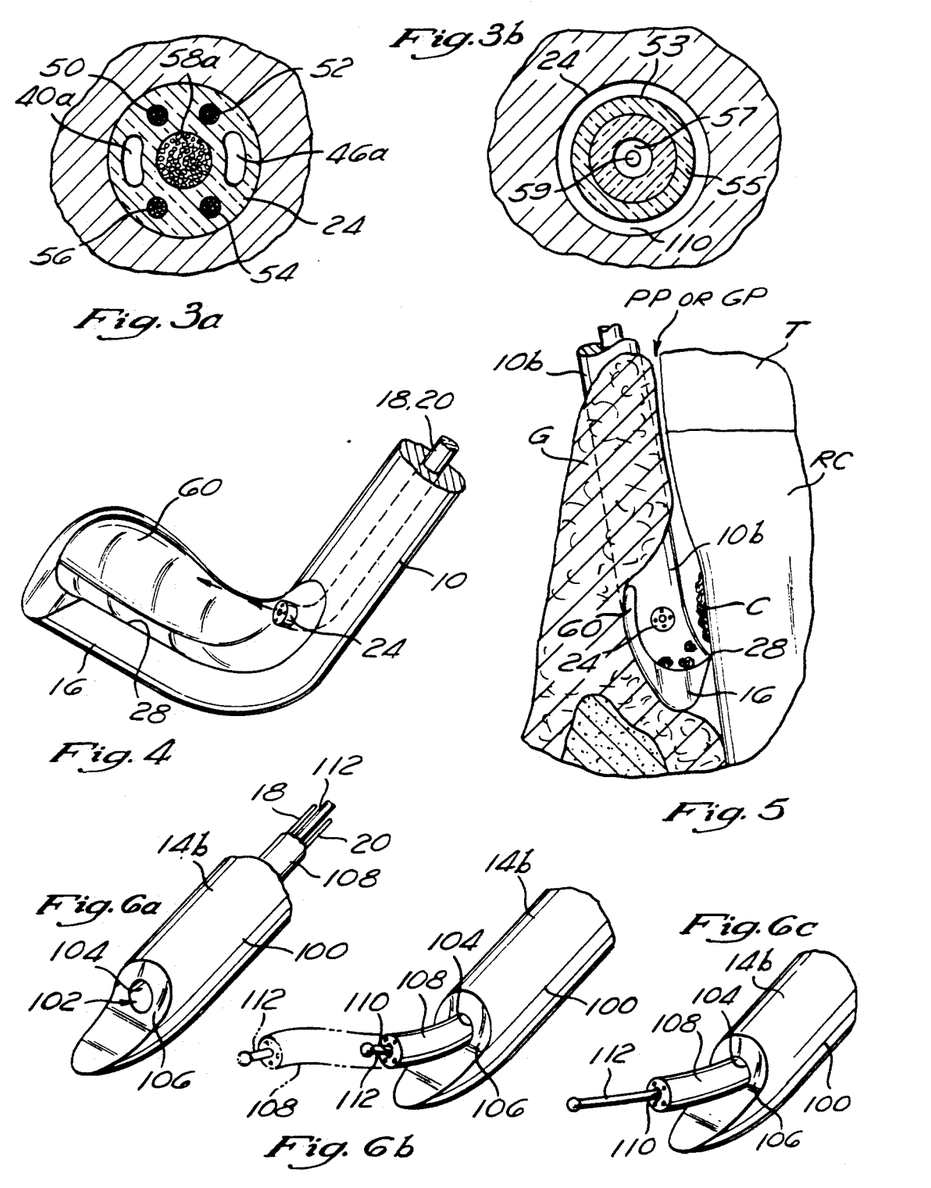
FIG. 3a is a plan view of one embodiment of an optical head usable in instruments of the present invention.
FIG. 3b is a plan view of an alternative embodiment of an optical head usable in instruments of the present invention.
FIG. 4 is an enlarged perspective view of the distal shank and blade portions of a hand curette instrument of the present invention incorporating an optional gingival tissue dilator member.
FIG. 5 is a schematic diagram of a portion of the human dental anatomy showing the instrument of FIG. 4 in its operative disposition within the periodontal pocket or crevice.
FIG. 6a is a perspective view of an ultrasonic or sonic instrument of the present invention having endoscopic viewing apparatus and ultrasonic probe elements which are fully retracted into the body of the instrument.
FIG. 6b is a perspective view of an ultrasonic or sonic instrument of the present invention having endoscopic viewing apparatus and ultrasonic probe components partially advanced out of the distal end of the instrument.
FIG. 6c is a perspective view of an ultrasonic or sonic instrument of the present invention having an endoscopic viewing apparatus and an ultrasonic probe fully advanced out of the distal end of the instrument.

One example of an optical head 24 shown in FIG. 3a comprises four separate illuminating ports 50, 52, 54, 56. In such embodiment, the first (illuminating) optical fiber bundle 18 is split into four separate groups of illuminating fibers such that the distal ends of the four separate groups of the illuminating optical fibers will terminate at the four illuminating lens member or light output ports 50, 52, 54, 56 within the distal head 24a. A central lens or image receiving port 58a is formed within the optical head 24a. Such lens or image receiving port 58 may comprise suitable type of lens or other optical apparatus capable of causing the second (image receiving) optical fiber group or bundle 20 to view and collect an optical image of the tooth surfaces lying adjacent to and ahead of the leading surface 28 of the working part or blade 16 of the instrument. The distal ends of the second (optical image transmitting) optical fiber bundle 20 terminate within the lens or image receiving port 58 of the optical head 24a.

The optical head 24a shown in FIG. 3a further incorporates an optional infusion fluid outlet port 46a as well as an optional suction or aspiration port 40a. The optional infusion fluid outlet port 46a and/or aspiration or suction port 40a need not necessarily be positioned within the optical head 24 and may be positioned at other points on the instrument 10. In fact, the positioning of the optional fluid outlet port 46a and/or optional aspiration port 58a may be located relative to the optical head 24a so as to maximize or optimize the ability to continuously or intermittently clear the optical field of blood and/or debris so as to maximize the ability of the instrument 10 to endoscopically visualize the tooth surface(s) being treated.

Another alternative configuration of the optical head 24 is shown in FIG. 3b. As shown in FIG. 3b, the optical head 24 may comprise concentric inner and outer optical fiber bundles such that the first (illuminating) optical fiber bundle 18 surrounds the second (image transmitting) optical fiber bundle 20 and whereby such first 18 and second 20 optical fiber bundles terminate at the optical head 24 in an outer circular illumination outlet port or lens 53 and an inner circular image receiving port or lens 55. A space or lumen 110 may surround the first and second optical fiber bundles to provide a passageway for infusion of irrigant solutions, antibacterial solutions, anesthetic solutions or other fluids and/or aspiration of blood or debris. Additionally, an inner lumen 57 extends longitudinally through the instrument and opens through the center of the optical head 24 as shown in FIG. 3b. An optional laser bundle, ultrasonic probe, or other member 59 may be passed or inserted through the central lumen 57 as shown in FIG. 3b. For example, such optional member 59 may comprise a sonic or ultrasonic transmitting wire or probe which may be longitudinally extended through the instrument 10 such that the ultrasonic or sonic wire or probe is extendable out of and/or retractable into the central lumen 57. Such sonic/ultrasonic wire or probe may be utilized to effect ultrasonic cleaning or debridement of subgingival tooth surfaces.

Various other configurations and designs of the optical head 24 may be utilized to effect the desired endoscopic function of the present invention. At the very least, such optical head will include means for projecting illuminating light onto the subgingival tooth surfaces and means for receiving and transmitting an optical image from such subgingival tooth surfaces. Optionally, any instrument or probe of the present invention may incorporate, as part of the optical head 24, or elsewhere, one or more (a) lumen(s) for infusion of fluids; (b) one or more lumen(s) for aspiration of fluids/debris; (c) one or more utility lumen(s) for insertion and/or retraction of ultrasonic/sonic transmission wires or probes or other instruments; and (d) one or more additional optical fiber bundles and/or lenses for transmission and projection of laser energy onto the gingival sulcus or periodontal pocket.

In embodiments which incorporate additional optical fiber bundles and/or lenses for transmission and projection of laser energy, such additional optical fiber bundles or other means for transmitting laser energy may be incorporated into the optical fiber passageways or lumens wherein the light transmitting and/or optical image transmitting fibers are found. Alternately, such laser transmitting optical fiber bundles or other laser transmitting apparatus may be passed through a separate hollow lumen 40 so as to project laser energy out of a distal opening (i.e., aperture 46) and onto the desired subgingival anatomical structures. In such embodiments, the laser image transmitting apparatus may comprise an elongate bundle of optical fibers having a first refractive index and increased within a surrounding envelope or shell having a second refractive index greater than said first refractive index such that laser energy will transmitted longitudinally through the optical fiber bundle. The proximal end of the laser transmitting optical fiber bundle is operatively connectable to or interfaceable with a separate laser source. The distal end of such laser transmitted optical fiber bundle may terminate at an aperture or lens located within the optical head of the instrument or at a separate location such as a distal aperture (e.g., aperture 40). When connected to an external laser energy source, laser energy will pass through the laser transmitting optical fiber bundle or other laser transmitting wave guide member so as to be projected from or out of an aperture lens or other laser outlet port located on or near the distal portion of the instrument, thereby passing laser energy onto the subgingival tooth surfaces or tissues.

One type of laser device which may be incorporated into the instrument of the present invention is a neodymium/yttrium-aluminum-garnet (syn: "Nd-yac") laser such as that available commercially as dlase-300 (American Dental Laser, Birmingham, Mi.). Such neodymium/yttrium-aluminum-garnet laser is passable through an optical fiber bundle and, thus, in embodiments incorporating such laser, the laser transmission means may incorporate an optical fiber bundle of the above-described character.

Other types of laser apparatus may also be incorporated into the devices of the present invention. For example, carbon dioxide lasers may be passed along appropriate types of carbon dioxide wave guides or carbon dioxide laser transmitting members known in the art.

It will be appreciated by those skilled in the art that various other configurations of the optical head 24 may be incorporated into the instrument 10 of the present invention. For example, the optical fibers of the first 18 and second 20 optical fiber bundles may, in actuality, be combined, fused, intermingled, juxtapositioned or otherwise arranged as a single group or single bundle of fibers wherein both the image transmitting and illuminating fibers are disposed.

In many cases, especially those in which periodontal treatment has successfully lessened the severity of gingival inflammation, the gingiva will lie in close proximity to or direct abutment with the subgingival tooth surfaces. In such cases the width of the gap or space between the tooth surface and the adjacent gingiva may be very small (e.g. 0–1 mm). Accordingly, the instrument 10 of the present invention may incorporate an optional dilator surface or dilator projection 60. One example of the invention incorporating a dilator projection 60 is shown in FIGS. 4 and 5. As shown, the dilator projection 60 may comprise a lip member or projection which extends in a generally proximal direction from one side of the leading edge 28 of the working part or blade 16 of the instrument 10. Such dilator projection 60 is preferably shaped in a slightly rounded or blunt configuration so as to minimize or avoid traumatization of the gingiva G. The dilator projection 60 is preferably sized and configured to spread and hold the gingiva G away from the tooth surface over a region or area of approximately several square centimeters ahead of the leading edge 28 of the working part or blade 16, thereby preventing the gingiva G from interfering with visualization of the tooth surface within such region or area ahead of the leading edge 28 of the working part or blade 16.

As shown, the optical head 24 of the device may be positioned in relation to the dilator projection 60 such that the dilator projection 60 shields the optical head 24, thereby preventing direct contact between the gingiva G and the optical head 24. FIG. 5 illustrates the manner in which an instrument 10b having an optional dilator projection 60 is utilized to remove dental calculus C from the outer root surface of a tooth T without surgical excision of the gingiva G.

The working part or blade 16 of the hand instrument 10 may comprise a curette blade as shown in FIGS. 2 and 4, or any other type of working part or blade presently or hereafter used to scrape or abrade subgingival tooth surfaces, including but not limited to those known in the art as hoes, sickles, chisels or files.

ii. An Ultrasonic or Sonic Instrument

Another embodiment of the invention comprises an ultrasonic or sonic instrument 100. The presently preferred ultrasonic/sonic instrument of the invention comprises an elongate handle and a reduced diameter shank such as the handle 12 and shank 14 of the hand instrument shown in FIG. 2. However, the presently preferred ultrasonic instrument differs from the hand instrument of FIG. 2 in that a central lumen or bore 102 extends longitudinally through the handle and shank portions of the device. The distal end of the lumen 102 opens through an aperture 104 at the distal end of the shank 14b of the instrument 100. In the embodiment shown, the shank 14b terminates in a blunt rounded distal tip having a notch 106 formed therein, with the aperture 104 being disposed within said notch 106. An elongate core member 108 is slidably disposed within lumen 102 such that the core member 108 may be alternately advanced out of and retracted into the distal end aperture 104 of lumen 102 as shown in FIGS. 6a, 6b and 6c respectively. The core member 108 may be formed of deformable plastics or metals having sufficient shape memory properties to permit the distal end of said core member 108 to assume a substantially straight configuration when retracted into lumen 102 but to assume a predetermined curved or bent configuration (phantom lines on FIG. 6b) when the distal portion of the core member is extended out of the distal end aperture 104 of lumen 102. Such shape memory or resiliency of the core member 108 will permit the operator of the device to pre-form or pre-shape the core member in a manner that will enable it to pass over obstructions or in a manner that will enable it to reach hard to access areas within the dental anatomy.

A hollow wave guide lumen 110 extends longitudinally through core member 108. An ultrasound/sound transmission wire or wave guide 112 is positioned within wave guide lumen 110. It is preferable that the outer diameter or outer dimension of the wave guide 112 be slightly smaller than the inner diameter or inner cross-dimension of the wave guide lumen 110 such that coolant liquid may be continuously or intermittently infused through lumen 110 around wave guide 112. Such coolant liquid will serve to cool the ultrasound transmission member 112 when ultrasonic energy is being passed therethrough. Additionally, liquid may be infused through lumen 110 at a sufficient rate to provide a liquid environment at the point of contact between the ultrasonic cleaning and debridement of the tooth surface. Additionally, liquid infused through lumen 110 may serve to irrigate or lavage the periodontal pocket PP so as to wash away blood or debris which may interfere with endoscopic visualization of the operative site.

In the embodiment shown in FIGS. 6a, 6b and 6c, the core member 108 may be slidably disposed within lumen 102 such that the core member is physically extendable out of and/or retractable into lumen 102. Any suitable servo motor arrangement or other mechanical means for extending and retracting the core member 108 may be attached to the proximal end of the core member and positioned outside of the body so as to permit the operator to control the degree of extension/retraction of the core member 108 out of and/or into lumen 102.

Similarly, the sonic or ultrasonic transmission wire or wave guide 112 may be slidably disposed within lumen 110 and attached to any suitable extension/retraction means such as a mechanical servo motor or other device positionable outside the patient's body and attachable to the proximal end of the transmission wire or wave guide 112 such that the operator may effect controlled extension and/or retraction of the transmission wire or wave guide 112 within lumen 110.

Controlled extension/retraction of core member 108 and/or wave guide 112 enables the operator of the device to position the bulbus tip or probe member on the distal end of the transmission wire or wave guide 112 against the subgingival tooth surface at a desired position to effect the intended removal or disintegration of subgingival plaque or calculus.

Sonic or ultrasonic devices of the present invention may optionally include one or more laser transmitting optical fiber bundles or other laser wave guides extending longitudinally through the instrument body and terminating at a distal port lens or other laser outlet opening positioned on the instrument such that laser energy cast out of said outlet opening will contact tissues or other anatomical structures within the gingival sulcus or periodontal pocket when the probe member of the invention is inserted therein. The specific construction, placement and/or type of the laser transmitting elements which may be included in the sonic or ultrasonic instruments of the present invention include all of those described with respect to the presently preferred "hand instruments" described in (i) here above.

iii. A Subgingival Endoscopic Probe

In addition to the above-described embodiments of the invention wherein the endoscopic looking device is incorporated into the body of an instrument (e.g. a hand instrument, an ultrasonic instrument or a rotating instrument) used to perform subgingival scaling and root planing procedures, the device of the present invention may alternatively be formed as a separate subgingival endoscopic probe 300. The subgingival endoscopic probe is insertable into the periodontal pocket PP separately from any instrument(s) used to conduct the desired subgingival scaling and root planing procedures. The probe may comprise an elongate handle such as the handle 12 of the embodiment shown in FIG. 2. A probe member 300 is attached to and extends forward from the distal end of such handle 12. The probe member 300 may be of straight configuration, or may be curved or contoured in any desired manner so as to fit easily into the periodontal pocket PP. The distal end 302 of the probe member 300 is preferably of blunt configuration so as to avoid traumatization of the gingival tissues when the probe 300 is inserted into the periodontal pocket PP.

Figures 7, 7A, 7B:
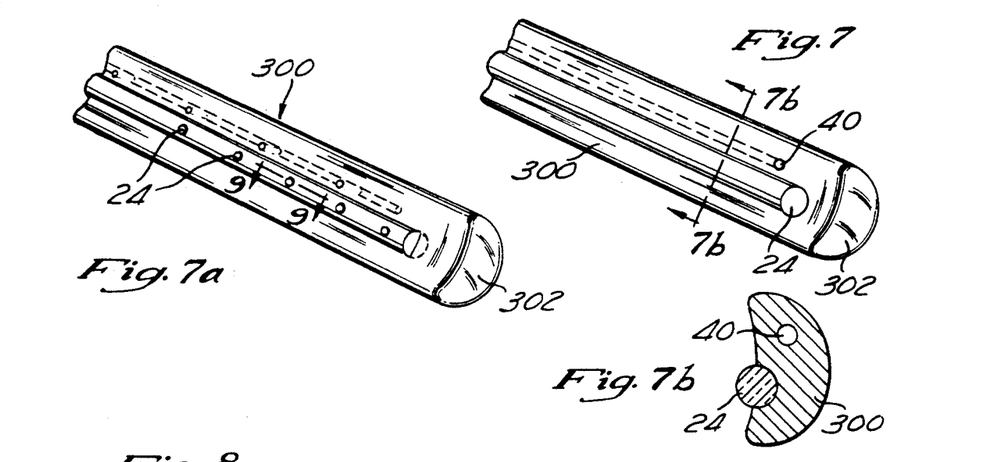
FIG. 7 is a perspective view of an alternative embodiment of the present invention comprising a blunt tip subgingival endoscopic probe.
FIG. 7a is a perspective view of a modified version of the blunt tipped probe instrument shown in FIG. 7 incorporating multiple fluid infusion ports and multiple optical heads.
FIG. 7b is a cross-sectional view through line 7b—7b of FIG. 7.

The first (illuminating) optical fiber bundle 18c and the second (image transmitting) optical fiber bundle 20c extend through the handle 12, through the probe 300 and terminate in at least one illumination port formed on the body of the probe.

Figures 8, 9:
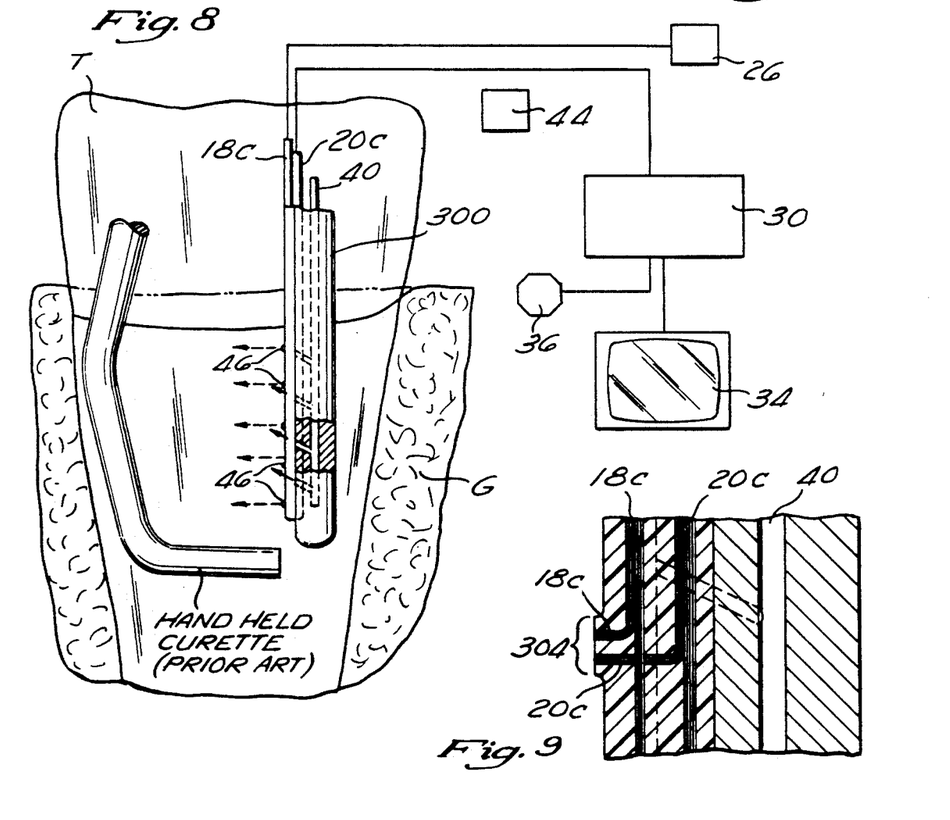

In the probe embodiment of the invention shown in FIGS. 7a, 8 and 9 multiple optical heads are positioned along the lateral edge or side of the probe 300. Some of the optical fibers within each of the first and second optical fiber bundles 18c and 20c diverge from the main optical fiber bundles 18c and 20c and terminate in each optical head 304.

The endoscopic probe of the present invention may optionally include one or more laser transmitting optical fiber bundles or other laser wave guides extending longitudinally through the probe body and terminating at a distal port lens or other laser outlet opening positioned on the probe such that laser energy cast out of said outlet opening will contact tissues or other anatomical structures within the gingival sulcus or periodontal pocket when the probe member of the invention is inserted therein. The specific construction, placement and/or type of the laser transmitting elements which may be included in the endoscopic probe of the present invention include all of those described with respect to the presently preferred "hand instruments" described in (i) here above.

iv. A Preferred Method for Performing Subgingival Procedures Under Endoscopic Visualization The method of the present invention broadly comprises the step of inserting an endoscopic viewing device between the free gingiva and subgingival tooth surfaces and utilizing such endoscopic viewing device to direct visualization of the subgingival tooth surfaces and/or subgingival tissues.

The method of the present invention is useable to endoscopically visualize, guide, monitor or assess any type of treatment procedure directed to subgingival tooth surfaces and/or subgingival tissues. Examples of treatment procedures in which the method of the present invention may be employed include, but are not limited to, (a) procedures for removing deposits of plaque or calculus from subgingival tooth surfaces, (b) procedures for resecting and removing subgingival granulation tissue, (c) procedures for seeding or implanting alveolar bone and the procedures for chemically treating or otherwise preparing root surfaces to facilitate connective tissue (e.g., ligamentous) attachment thereto.

Figure 10:
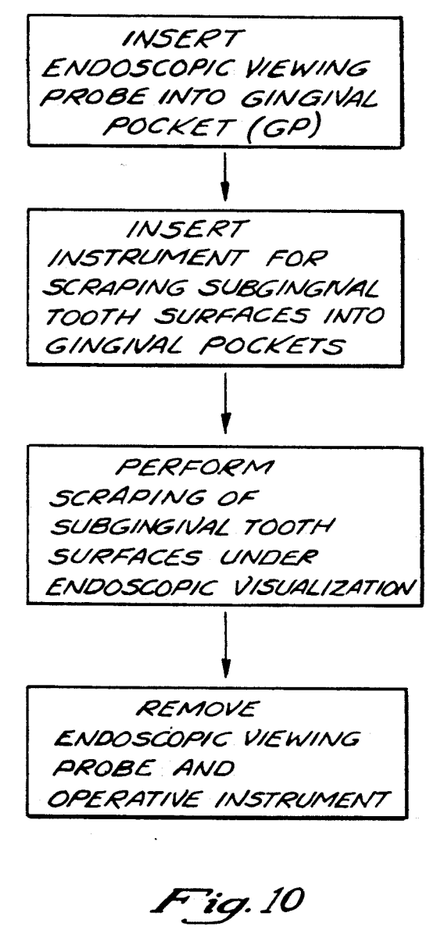
FIG. 10 is a block diagram of a method of the present invention wherein the endoscopic viewing probe is separate from the instrument utilized to treat the subgingival tooth surfaces.

In accordance with one embodiment of the method, an instrument, such as the curette shown in FIG. 2, incorporating (a) a working part or blade and (b) an endoscopic image transmitting means such as fiber optic light and image transmitting bundles, is inserted into the periodontal pocket and utilized to effect the desired subgingival scaling and root planing. The specific steps of such method, as shown in the flow diagram of FIG. 10, comprise (a) inserting an endoscopic viewing probe into the periodontal pocket PP; (b) inserting into the periodontal pocket an instrument for scraping subgingival tooth surfaces; (c) utilizing the instrument to perform the desired scraping of the subgingival tooth surfaces; (d) utilizing the endoscopic viewing probe to view the subgingival tooth surfaces upon which the scraping procedure is carried out and (e) removing the endoscopic viewing probe and the operative instrument from the periodontal pocket.

It will be appreciated that, in accordance with the basic method of the invention, the endoscopic viewing probe may be formed separately from the instrument for scraping the subgingival tooth surfaces.

Figure 11:
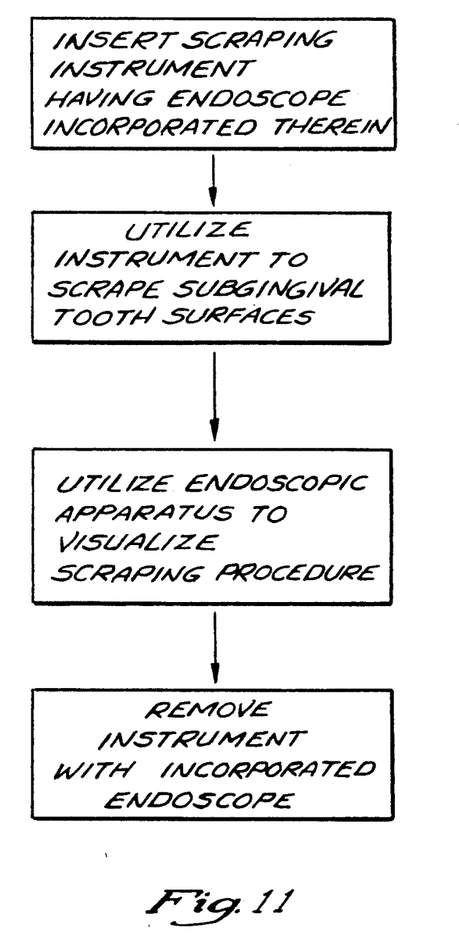
FIG. 11 is a block diagram of a method of the present invention wherein the endoscopic viewing apparatus is incorporated into the instrument utilized to treat the subgingival tooth surfaces.

In one specific embodiment of the method of the present invention, the endoscopic viewing probe may be incorporated into the body of the instrument for scraping the subgingival tooth surfaces and the method may comprise the steps of: (a) inserting the scraping instrument/endoscopic probe into the periodontal pocket; (b) utilizing the scraping instrument/endoscopic probe to scrape subgingival tooth surfaces while endoscopically viewing said tooth surfaces; and (c) removing said scraping instrument/endoscopic probe from the periodontal pocket.

The individual steps of this more specific embodiment of the method of the present invention are shown in the flow diagram of FIG. 11.

It will be appreciated that the scraping instrument into which the endoscopic probe is incorporated in the method of FIG. 11 may comprise any type of hand, ultrasonic or rotating instrument usable for the purpose of effecting subgingival scraping procedure (e.g. scaling and root planing) procedures.

The invention has been described herein with reference to presently preferred embodiments of the device and specific examples of the method. None of the descriptions or examples set forth herein are intended to limit the scope of the invention. In fact, it is expected that persons of skill in the art will recognize numerous alternatives, additions and modifications which may be applied to the specific embodiments and examples described herein. It is intended that all such alternatives, additions and modifications be included within the scope of the scope of the present invention as defined by the following claims and the equivalents thereof.

What is claimed is:

1. A dental instrument for removing deposits of dental plaque and calculus from subgingival tooth surfaces, under endoscopic visualization, said instrument comprising:
   (a) an elongate handle having a proximal end, a distal end, and a first cross-sectional area;
   (b) a shank extending from the distal end of said elongate handle, said shank having a cross-sectional area smaller than the cross-sectional area of said handle;
   (c) a working part extending from said shank, said working part being sized and configured to be insertable between the free gingiva and the subgingival tooth surfaces without surgical cutting of the gingiva, and sized and configured to be useable to remove plaque and calculus deposits from said subgingival tooth surfaces;
   (d) a light transmission means extending longitudinally through at least a portion of said instrument, said light transmission means having a proximal end which is connectable to a light source, said light transmission means extending distally from said proximal end thereof to at least one illumination outlet port located adjacent the working part of said instrument;
   (e) an optical image transmission means extending longitudinally through at least a portion of said instrument, said optical image transmission means having a proximal end which is connectable to an external image viewing apparatus, said optical image transmission means extending distally from said proximal end thereof to at least one optical image receiving port.

2. The instrument of claim 1 wherein said working part comprises a curette blade sized and configured to scrape deposits from subgingival tooth surfaces.

3. The instrument of claim 1 wherein said working part comprises a hoe, sized and configured to scrape deposits from subgingival tooth surfaces.

4. The instrument of claim 1 wherein said working art comprises a sickle, sized and configured to scrape deposits from subgingival tooth surfaces.

5. The instrument of claim 1 wherein said working part comprises a file, sized and configured to scrape deposits from subgingival tooth surfaces.

6. The instrument of claim 1 wherein said light transmission means comprises optical fibers.

7. The instrument of claim 1 wherein said light transmission means comprises at least one bundle of optical fibers.

8. The instrument of claim 1 wherein said light transmission means comprises an inner core having a first refractive index and an outer shell surrounding said inner core, said outer shell having a second refractive index different from said first refractive index such that light will be conducted longitudinally along said inner core.

9. The instrument of claim 1 wherein said image transmission means comprises optical fibers.

10. The instrument of claim 1 wherein said image transmission means comprises at least one bundle of optical fibers.

11. The instrument of claim 1 wherein said working part has a leading edge and wherein said illumination outlet port and said optical image receiving port are located adjacent the leading edge of said working part to permit endoscopic viewing of the subgingival tooth surfaces immediately ahead of said leading edge.

12. The instrument of claim 1 further in combination with an external light source connected to said light transmission means and operative to send illuminating light through said light transmission means.

13. The instrument of claim 1 further in combination with an external image viewing device connected to said image transmission means and operative to receive and display an optical image transmitted through said image transmitting means.

14. The instrument of claim 13 wherein said external image viewing device comprises an eyepiece.

15. The instrument of claim 13 wherein said external image viewing device comprises a video monitor.

16. The instrument of claim 13 wherein said external image viewing device comprises a television monitor.

17. The instrument of claim 13 further comprising a recording device operatively connected to said image viewing device for storing and recording the images received by said image viewing device.

18. The instrument of claim 1 further comprising a magnifying means for magnifying the image transmitted through said image transmitting means.

19. The instrument of claim 1 further comprising at least one dilator member extending from said instrument adjacent the working part thereof; said dilator member being sized and configured to widen portions of the gingival sulcus by separating the gingival tissue away from the subgingival tooth surfaces.

20. The instrument of claim 19 wherein said dilator member is further sized and configured to separate the gingival tissue away from the adjacent tooth surfaces within the field of said optical image receiving port to allow endoscopic viewing of the subgingival tooth surfaces adjacent said image receiving port without obstruction by the gingival tissue.

21. The instrument of claim 1 wherein said illumination outlet port comprises a lens.

22. The instrument of claim 1 wherein said optical image receiving port comprises a lens.

23. The instrument of claim 1 further comprising at least one infusion lumen extending longitudinally through said instrument and an infusion aperture located adjacent said working part permit infusion of fluid therethrough.

24. The instrument of claim 1 further comprising at least one aspiration lumen extending longitudinally through said instrument and terminating in at least one aspiration aperture located adjacent said working part to permit aspiration of fluid therethrough.

25. The instrument of claim 1 further comprising:
a laser energy transmission means extending longitudinally through at least a portion of said instrument, said laser energy transmission means having a proximal end which is connectable to a laser energy source, said laser energy transmission means extending distally from the proximal end thereof to at least one laser energy outlet port positioned on said instrument such that laser energy passing out of said laser energy outlet port will enter the area between the subgingival tooth surfaces and free gingiva when said instrument is inserted between said subgingival tooth surfaces and said free gingiva.

26. The device of claim 25 wherein said laser energy is a type of laser energy transmissable through an optical fiber and wherein said laser energy transmission means comprises an optical fiber bundle.

27. The device of claim 26 further in combination with a neodymium/yttrium-aluminum-garnett laser energy generator connectable to the proximal end of said laser transmission means.

28. The device of claim 25 wherein said laser transmission means comprises a wave guide formed of material capable of transmitting a carbon dioxide laser.

29. The device of claim 28 further in combination with carbon dioxide laser generating device attachable to the proximal end of said laser energy transmission means.

30. A method of removing material deposited on subgingival tooth surfaces without surgical cutting of the gingiva, said method comprising the steps of:
(a) inserting an endoscopic viewing instrument between the free gingiva and the subgingival tooth surfaces upon which said material is deposited;
(b) inserting, between the free gingiva and subgingival tooth surfaces, an operative instrument for removing deposited material from said subgingival tooth surfaces;
(c) utilizing said operative instrument to remove deposited material from said subgingival tooth surfaces; and
(d) utilizing said endoscopic instrument to visualize the subgingival tooth surfaces to visually verify the removal of said deposited material from the subgingival tooth surfaces by said operative instrument.

31. The method of claim 30 further comprising the step of:
   (e) utilizing said endoscopic instrument to guide the placement and movement of said operative instrument during removal of said deposited material from said subgingival tooth surfaces.

32. The method of claim 30 wherein said endoscopic instrument and said operative instrument are combined within a single endoscopic/operative instrument which incorporates both (i) an endoscopic viewing instrument component for and (ii) an operative instrument component for removing deposited material from said subgingival tooth surfaces, and wherein steps (a) and (b) of said method are simultaneously accomplished by inserting said endoscopic/operative instrument into said gingival sulcus, and wherein steps (c) and (d) further comprise:
   (c) utilizing the operative component of said endoscopic/operative instrument to remove deposited material from said subgingival tooth surfaces; and
   (d) utilizing the endoscopic component of said endoscopic/operative instrument to visualize said subgingival tooth surfaces and to thereby visually verify the removal of said deposited material from the subgingival tooth surfaces by the operative component of said instrument.

33. The method of claim 32 further comprising the step of:
   (e) utilizing the endoscopic component of said endoscopic/operative instrument to guide the placement and movement of said operative component thereof during removal of said deposited material from said subgingival tooth surfaces.

34. The method of claim 30 further comprising the step of:
   infusing at least one fluid into the area between the free gingiva and the subgingival tooth surfaces to clear debris from said area.

35. The method of claim 30 further comprising the step of:
   aspirating at least one fluid from the area between the free gingiva and the subgingival tooth surfaces to clear debris from said area.

36. The method of claim 30 further comprising the step of:
   inserting, into the area between the free gingiva and the subgingival tooth surfaces, a means for separating the free gingiva from the opposing tooth surfaces so as to facilitate endoscopic viewing of said tooth surfaces without obstruction by said gingiva.

37. An endoscopic dental probe insertable between the free gingiva and the subgingival tooth surfaces to effect endoscopic viewing of subgingival tooth surfaces without surgical cutting of the gingiva, said probe comprising:
   (i) an elongate probe body having a proximal end and a distal end, said distal end being sized and configured for insertion between the free gingiva and the subgingival tooth surfaces;
   (ii) an endoscopic viewing apparatus incorporated within said elongate probe body, said endoscopic viewing apparatus comprising:
      (a) a light transmission means extending longitudinally through at least a portion of said elongate probe body, said light transmission means having a proximal end which is connectable to a light source, said light transmission means extending distally from said proximal end thereof to at least one illumination outlet port located on the portion of said elongate probe body which is insertable between the free gingiva and the subgingival tooth surfaces;
      (b) an optical image transmission means extending longitudinally through said elongate probe, said optical image transmission means having a proximal end which is connectable to an external image viewing apparatus, said optical image transmission means extending distally from said proximal end thereof to at least one optical image receiving port located on the portion of said probe insertable between the free gingiva and the subgingival tooth surfaces; and
   wherein said light transmission means comprises an inner core having a first refractive index and an outer shell surrounding said inner core, said outer shell having a second refractive index different from said first refractive index such that light will be conducted along said inner core.

38. The device of claim 37 further comprising:
   a laser energy transmission means extending longitudinally through at least a portion of said instrument, said laser energy transmission means having a proximal end which is connectable to a laser energy source, said laser energy transmission means extending distally from the proximal end thereof to at least one laser energy outlet port positioned on said instrument such that laser energy passing out of said laser energy outlet port will enter the area between the subgingival tooth surfaces and free gingiva when said instrument is inserted between said subgingival tooth surfaces and said free gingiva.

39. The device of claim 38 wherein said laser energy is a type of laser energy transmissable through an optical fiber and wherein said laser energy transmission means comprises an optical fiber bundle.

40. The device of claim 39 further in combination with a neodymium/yttrium-aluminum-garnet laser energy generator connectable to end of said laser transmission means.

41. The device of claim 38 wherein said laser transmission means comprises a wave guide formed of material capable of transmitting a carbon dioxide laser.

42. The device of claim 41 further in combination with a carbon dioxide laser generating device attachable to the proximal end of said laser energy transmission means.

43. The instrument of claim 38 further in combination with a sonic energy source.

44. The instrument of claim 38 further in combination with an ultrasonic energy source.

45. The instrument of claim 38 wherein said core member is formed of deformable material having sufficient shape memory properties to permit at least the distal end of said core member to assume a substantially straight configuration when it retracted into said bore but to assume a predetermined curved or bent configuration when extended out of the distal aperture of said bore.

46. The device of claim 38 further comprising at least one infusion fluid lumen extending longitudinally through said instrument and opening through at least one infusion fluid outlet aperture located on said instrument to permit infusion of fluid through said instrument into the area between the free gingiva and the subgingival tooth surfaces.

47. The instrument of claim 38 further comprising at least one aspiration fluid aperture extending longitudinally through said instrument and opening through at least one aspiration fluid inlet aperture located on said instrument to permit aspiration of fluid from the area between the free gingiva and said subgingival tooth surfaces.

48. The instrument of claim 38 further comprising:
(k) means for alternately a (i) extending said core member out of said distal aperture and (ii) retracting said core member into said distal aperture.

49. An endoscopic dental probe insertable between the free gingiva and the subgingival tooth surfaces to effect endoscopic viewing of subgingival tooth surfaces without surgical cutting of the gingiva, and probe comprising:
   an elongate probe body having a proximal end and a distal end, said distal end being sized and configured for insertion between the free gingiva and the subgingival tooth surfaces;
   an endoscopic viewing apparatus incorporated within said elongate probe body, said endoscopic viewing apparatus comprising:
      (a) a light transmission means extending longitudinally through at least a portion of said elongate probe body, said light transmission means having a proximal end which is connectable to a light source, said light transmission means extending distally from said proximal end thereof to at least one illumination outlet port located on the portion of said elongate probe body which is insertable between the free gingiva and the subgingival tooth surfaces;
      (b) an optical image transmission means extending longitudinally through said elongate probe, said optical image transmission means having a proximal end which is connectable to an external image viewing apparatus, said optical image transmission means extending distally from said proximal end thereof to at least one optical image receiving port located on the portion of said probe insertable between the free gingiva and the subgingival tooth surfaces; and
      (c) wherein said image transmission means comprises an inner core having a first refractive index and an outer shell surrounding said inner core, said outer shell having a second refractive index different from said first refractive index such that light will be conducted along said inners.

50. An endoscopic dental probe insertable between the free gingiva and the subgingival tooth surfaces to effect endoscopic viewing of subgingival tooth surfaces without surgical cutting of the gingiva, said probe comprising;
   an elongate probe body having a proximal end and a distal end, said distal end being sized and configured for insertion between the free gingiva and the subgingival tooth surfaces;
   an endoscopic viewing apparatus incorporated within said elongate probe body, said endoscopic viewing apparatus comprising:
      (a) a light transmission means extending longitudinally through at least a portion of said elongate probe body, said light transmission means having a proximal end which is connectable to a light source, said light transmission means extending distally from said proximal end thereof to at least one illumination outlet port located on the portion of said elongate probe body which is insertable between the free gingiva and the subgingival tooth surfaces;
      (b) an optical image transmission means extending longitudinally through said elongate probe, said optical image transmission means having a proximal end which is connectable to an external image viewing apparatus, said optical image transmission means extending distally from said proximal end thereof to at least one optical image receiving port located on the portion of said probe insertable between the free gingiva and the subgingival tooth surfaces; and
      (c) at least one dilator member extending from said probe; said dilator member being sized, configured and positioned to separate the gingival tissue away from the subgingival tooth surfaces.

51. The instrument of claim 50 wherein said dilator member is further sized and configured to separate the gingival tissue away from the adjacent tooth surfaces within the field of said optical image receiving port to allow endoscopic viewing of the subgingival tooth surfaces adjacent said image receiving port without obstruction by the gingival tissue. core member out of said distal aperture and (ii) retracting said core member into said distal aperture.

52. The instrument of claim 51 wherein said illumination outlet port comprises a lens.

53. The instrument of claim 51 wherein said optical image receiving port comprises a lens.

54. The device of claim 51 further comprising:
   a laser energy transmission means extending longitudinally through at least a portion of said instrument, said laser energy transmission means having a proximal end which is connectable to a laser energy source, said laser energy transmission means extending distally from the proximal end thereof to at least one laser energy outlet port positioned on said instrument such that laser energy passing out of said laser energy outlet port will enter the area between the subgingival tooth surfaces and free gingiva when said instrument is inserted between said subgingival tooth surfaces and said free gingiva.

55. The device of claim 54 wherein said laser energy is a type of laser energy transmissable through an optical fiber and wherein said laser energy transmission means comprises an optical fiber bundle.

56. The device of claim 55 further in combination with a neodymium/yttrium-aluminum-garnet laser energy generator connectable to the proximal end of said laser transmission means.

57. A sonic instrument for removing deposited material from subgingival tooth surfaces, under endoscopic visualization, said instrument comprising:
   (a) an elongate handle having a proximal, a distal end, and a first cross-sectional area;
   (b) a shank extending from a distal end of said elongate handle, said shank having cross-sectional area smaller than the cross-sectional area of said handle;
   (c) a hollow longitudinal bore extending through said elongate handle and through at least a portion of said shank and terminating in a distal aperture formed in said shank;
   (d) an elongate core member slidably disposed within the longitudinal bore of said instrument, said core member having a proximal end and a distal end, the distal end of said core member being alternately advanceable out of and retractable into said distal aperture;

(e) a hollow wave guide lumen extending longitudinally through said core member;

(f) a wave guide member extending longitudinally through said wave guide lumen, said wave guide member having a proximal end and a distal end, the proximal end of said wave guide member being attachable to a sonic wave transmission source;

(g) a tip member formed on the distal end of said wave guide member and extending beyond the distal end of said core member;

(h) said wave guide member and said tip member being configured and constructed such that, when the proximal end of said wave guide member is attached to a source of sonic or ultrasonic energy, said energy will be transmitted through said wave guide member and to said tip member;

(i) a light transmission means extending longitudinally through at least a portion of said instrument, said light transmission means having a proximal end which is connectable to a light source, said light transmission means extending distally from said proximal end thereof to at least one illumination outlet port positioned to cast illuminating light in the area of the distal tip of said instrument during operation thereof;

(j) an optical image transmission means extending longitudinally through at least a portion of said instrument, said optical image transmission means having a proximal end which is connectable to an external image viewing apparatus, said optical image transmission means extending distally from said proximal end thereof to at least one optical image receiving port positioned to receive an optical image form the area of the distal tip of said instrument during operation thereof.

58. The device of claim 57 wherein said laser transmission means comprises a wave guide formed of material capable of transmitting a carbon dioxide laser.

59. The device of claim 58 further in combination with a carbon dioxide laser generating device attachable to the proximal end of said laser energy transmission means.

60. The device of claim 57 wherein said instrument is an ultrasonic instrument and wherein said wave guide member is attachable to an ultrasound source.

61. A non-surgical method for visually assessing a periodontal treatment procedure directed to tooth surfaces or other anatomical structures lying below the intact nonincised gingiva said method comprising the steps of:

(a) inserting an endoscopic viewing apparatus into the sulcus between the intact nonincised free gingiva and the adjacent subgingival tooth surfaces; and (b) utilizing said endoscopic viewing apparatus to endoscopically visualize at least one anatomical structure which is concealed from external visualization by the intact nonincised gingiva.

62. The method of claim 61 wherein the step of "utilizing said endoscopic viewing apparatus to endoscopically visualize at least one anatomical structure of the periodontium" comprises:

utilizing said apparatus to view the subgingival tooth surfaces.

63. The method of claim 61 wherein the step of "utilizing said endoscopic viewing apparatus to endoscopically visualize at least one anatomical structure of the periodontium" comprises:

utilizing said apparatus to view subgingival tissue.

64. The method of claim 61 wherein steps (a) and (b) are carried out concomitantly with said treatment procedure so as to permit visualization of said treatment procedure while it is being carried out.

65. The method of claim 61 wherein steps (a) and (b) are carried out after completion of said treatment procedure to permit visual assessment of the efficacy of said treatment procedure.

66. The method of claim 61 wherein said periodontal treatment procedure comprises a procedure for removing deposits the plaque from subgingival tooth surfaces.

67. The method of claim 61 wherein said periodontal treatment procedure comprises a procedure for removing deposits of calculus from subgingival tooth surfaces.

68. The method of claim 61 wherein said periodontal treatment procedure comprises a procedure for resecting subgingival granulation tissue.

69. The method of claim 61 wherein said periodontal treatment procedure comprises a procedure for seeding alveolar bone.

70. The method of claim 61 wherein said periodontal treatment procedure comprises a procedure for delivering chemical treatment to the root surface.

71. An endoscopic dental probe insertable between the free gingiva and the subgingival tooth surfaces to effect endoscopic viewing of subgingival tooth surfaces without surgical cutting of the subgingival tooth surfaces without surgical cutting of the gingiva, said probe comprising:

an elongate probe body having a proximal end and a distal end, said distal end being sized and configured for insertion between the free gingiva and the subgingival tooth surfaces;

an endoscopic viewing apparatus incorporated within said elongate probe body, said endoscopic viewing apparatus comprising:

(a) a light transmission means extending longitudinally through at least a portion of said elongate probe body, said light transmission means having a proximal end which is connectable to a light source, said light transmission means extending distally from said proximal end thereof to at least one illumination outlet port located on the portion of said elongate probe body which is insertable between the free gingiva and the subgingival tooth surfaces;

(b) an optical image transmission means extending longitudinally through said elongate probe, said optical image transmission means having a proximal end which is connectable to an external image viewing apparatus, said optical image transmission means extending distally from said proximal end thereof to at least one optical image receiving port located on the portion of said probe insertable between the free gingiva and the subgingival tooth surfaces; and (c) at least one aspiration lumen extending longitudinally through said probe and terminating in at least one aspiration fluid inlet aperture to permit aspiration of fluid therethrough from the area between the free gingiva and the subgingival tooth surfaces.

72. The endoscopic dental probe of claim 37, 49, 50 or 71 wherein said image transmission means comprises at least one optical fiber.

73. The endoscopic dental probe of claim 37, or 94 further in combination with an external light source connected to said light transmission means and operative to send illuminating light through said light transmission means.

74. The endoscopic dental probe of claim 37, 49, 50, or 71 further in combination with an external image viewing device connected to said image transmission means and operative to receive and display an optical image transmitted to said image viewing device through said image transmitting means.

75. The endoscopic dental probe of claim 74 wherein said external image viewing device comprises an eyepiece.

76. The endoscopic dental probe of claim 74 wherein said external image viewing device comprises a video monitor.

77. The endoscopic dental probe of claim 37, 50 or 71 further in combination with a video recording device connected to said image transmission means to record images received through said image transmission means.

78. The endoscopic dental probe of claim 37, 49, 50 or 71 further comprising magnifying apparatus for magnifying the image transmitted through said image transmitting means.

79. The endoscopic dental probe of claim 37, 49, 50 or 71 further comprising at least one infusion lumen extending longitudinally through said probe and terminating in at least one infusion fluid outlet aperture to permit infusion of fluid through said probe into the area between the free gingiva and the subgingival tooth surfaces.

80. The endoscopic dental probe of claim 37, 49, 50 or 71 further comprising at least one aspiration lumen extending through said probe and terminating distally in at least one aspiration fluid inlet aperture to permit fluid to be aspirated through said probe from the area between the free gingiva and the subgingival tooth surfaces.

* * * * *